(12) United States Patent
Hettche et al.

(10) Patent No.: US 6,348,490 B1
(45) Date of Patent: *Feb. 19, 2002

(54) DOSAGE FORMS CONTAINING THIOCTIC ACID OR SOLID SALTS OF THIOCTIC ACID WITH IMPROVED RELEASE AND BIOAVAILABILITY

(75) Inventors: Helmut Hettche, Dietzenbach; Matthias Rischer, Maintal; Werner Sarlikiotis, Frankfurt, all of (DE)

(73) Assignee: Asta Medica Aktiengesellschaft (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/377,741

(22) Filed: Aug. 20, 1999

Related U.S. Application Data

(63) Continuation of application No. 08/800,239, filed on Feb. 12, 1997, now Pat. No. 5,990,152, which is a continuation of application No. 08/531,978, filed on Sep. 21, 1995, now abandoned.

(30) Foreign Application Priority Data

Sep. 22, 1994 (DE) .......................................... 44 33 764

(51) Int. Cl.⁷ ............................................ A61K 31/385
(52) U.S. Cl. ...................................................... 514/440
(58) Field of Search .......................................... 514/440

(56) References Cited

U.S. PATENT DOCUMENTS

| | | | | |
|---|---|---|---|---|
| 3,718,664 A | * | 2/1973 | Salat et al. | 260/327 |
| 5,281,722 A | * | 1/1994 | Blaschke et al. | 549/39 |
| 5,376,382 A | * | 12/1994 | Goede et al. | 424/464 |
| 5,990,152 A | * | 11/1999 | Hettche et al. | 514/440 |

FOREIGN PATENT DOCUMENTS

| | | |
|---|---|---|
| DE | 43 17 646 A1 | 12/1994 |
| DE | 43 43 593 A1 | 6/1995 |
| EP | 0 427 246 A2 | 5/1991 |
| EP | 0 427 247 A2 | 5/1991 |
| EP | 0 530 446 A2 | 3/1993 |

OTHER PUBLICATIONS

The Merck Index, 11th ed. Merck & Co., Inc. (NJ), p. 1469, cit. 9255, 1989.*

* cited by examiner

Primary Examiner—Raymond Henley, III
(74) Attorney, Agent, or Firm—Venable; Ann S. Hobbs

(57) ABSTRACT

Novel, advantageous dosage forms of thioctic acid and the enantiomers thereof together with thioctic acid salts are described. The pharmaceutical formulations according to the invention are used for the production of pharmaceutical dosage forms which release the active ingredient more rapidly and have greater bioavailability than previous forms.

4 Claims, No Drawings

DOSAGE FORMS CONTAINING THIOCTIC ACID OR SOLID SALTS OF THIOCTIC ACID WITH IMPROVED RELEASE AND BIOAVAILABILITY

This is a continuation of application Ser. No. 08/800,239, filed Feb. 12, 1997 now U.S. Pat. No. 5,990,152, which is a continuation of application Ser. No. 08/531,978, filed Sep. 21, 1995, now abandoned.

BACKGROUND OF THE INVENTION

1. Field of the Invention

The invention relates to pharmaceutical formulations of thioctic acid and the enantiomers thereof. Formulations according to the invention are used for the production of pharmaceutical dosage forms which release the active ingredient more rapidly and have greater bioavailability than previous dosage forms.

2. Description of the Related Art

Thioctic acid (α-lipoic acid) is chemically 1,2-dithiacyclopentane-3- valeric acid. The production of free R-thioctic acid is described, for example, in DE-OS 41 37 773.

Thioctic acid is a component of cell metabolism and is thus found in many plants and animals. It acts as one of the coenzymes during oxidative decarboxylation of pyruvate and other α-keto acids. Thioctic acid has been used for some time in various conditions, for example, inter alia, in liver conditions, in liver damage due to fungal poisoning and in diabetic and alcoholic polyneuropathy, a degeneration of the peripheral nerves which accompanies metabolic disorders.

The present invention relates to pharmaceutical formulations containing thioctic acid or solid salts of thioctic acid with improved bioavailability.

This invention relates not only to the racemic form, but also to the pure (R)- or (S)-thioctic acid as well as to mixtures of (R)- and (S)-thioctic acid of any desired composition. Of the pure optical isomers of thioctic acid (R- and S-form, i.e. R-thioctic acid and S-thioctic acid), unlike the racemate, the R-enantiomer has a predominantly anti-inflammatory action and the S-enantiomer has a predominantly anti-nociceptive action, wherein the anti-inflammatory action of the R-enantiomer is, for example, stronger than that of the racemate by a factor of 10.

The anti-nociceptive (analgesic) action of the S-enantiomer is, for example, stronger than that of the racemate by a factor of 6.

Thus, in comparison with the racemate, the enantiomers are much more specific and effective active ingredients.

The actions are described in EP 427 246 and EP 427 247 and in GbM 90 17 987.0 and EP 530 446.

A combination of thioctic acid with vitamins is described in EP 572 922.

R,S-Thioctic acid has a melting point of 60.5° C. R-Thioctic acid has a melting point of 50.6–50.7° C. Both are soluble at 25° C. in water at a rate of 12.14 mg/10 ml and in methanol, ethanol, chloroform, dimethylformamide and n-octanol at a rate of above 1000 mg/10 ml.

In comparison with parenteral dosage forms, orally administrable pharmaceutical preparations have a price advantage, which has a favorable effect on daily therapeutic costs. However, previous dosage forms of thioctic acid have the disadvantage of having relatively low bioavailability. Low bioavailability means that, on oral administration of the dosage form, in comparison with intravenous administration, relatively little of the unaltered active ingredient is found in the blood of the test subject or patient. As a consequence, oral administration of the medication cannot be as effective as intravenous administration of the active ingredient. There is thus an object of developing dosage forms which, together with good storage stability, have the greatest possible bioavailability.

SUMMARY OF THE INVENTION

The present invention provides dosage forms of thioctic acid and solid salts thereof having increased bioavailability in comparison with previous dosage forms. The increased bioavailability is surprisingly achieved by preparing the active ingredient in a form resistant to gastric juice, which, once it has passed into the duodenum, rapidly dissolves at the pH value of the intestinal juice. The pH value of the intestinal juice is 6.8 to 7.3. The active ingredient which may be used here is either the free thioctic acid or—more advantageously—a salt of thioctic acid.

The poor release of the active ingredient R-thioctic acid from the dosage forms prepared therefrom is disadvantageous. On release testing according to the *Deutsches Arzneibuch* [German pharmacopoeia], 10th edition (paddle agitator method) or USP XXII [United States pharmacopeia, 22nd Edition] with apparatus 2), release of the active ingredient from tablets according to Example 2a, using 0.06 N HCl as release medium at 37° C., is as follows:

after 15 minutes: 6%
after 30 minutes: 9%
disintegration time: <2 min.

This is in contrast with the behaviour of tablets prepared from the racemate of thioctic acid, which, with the same composition of the tablets, exhibit the following active ingredient release (method as above):

after 15 minutes: 99%
after 30 minutes: 100%
disintegration time: 2.5 min.

It was surprisingly found that when solid salts of R-thioctic acid were used to produce the tablets according to Example 3, good release values were again obtained (method as above):

after 15 minutes: 75%
after 30 minutes: 88%
disintegration time: <1 min.

Salt formers which may, for example, be considered are conventional bases or cations which are physiologically compatible in salt form. Examples of such substances are:

alkali or alkaline earth metals, such as sodium, potassium, calcium, magnesium;

ammonium hydroxide;

basic amino acids, such as, for example, ornithine, cystine, methionine, arginine and lysine;

amines of the formula N R1 R2 R3, in which the residues R1, R2 and R3 are identical or different and mean hydrogen, $C_1$–$C_4$ alkyl, such as, for example, methyl, ethyl, propyl, isopropyl, butyl, isobutyl, tert.-butyl, or $C_1$–$C_4$ oxyalkyl, such as, for example, mono- and diethanolamine, 1-amino-2-propanol, 3-amino-1-propanol;

alkylenediamines with an alkylene chain of 2 to 6 C atoms, such as, for example, ethylenediamine or hexamethylene-tetramine; and saturated cyclic amino compounds with 4 to 6 ring carbon atoms, such as, for example, piperidine, piperazine, pyrrolidone, morpholine; N-methylglucamine, creatine and tromethamine.

The salt formers have already been mentioned in the above-stated patents in general terms, but production of the salts and the particular suitability thereof for the production of certain dosage forms is not discussed. Liquid dosage forms with the tromethamine, lysine and ethylenediamine salt of R-thioctic acid are described in various patent applications, for example in EP 427 246, EP 427 247, EP 530 446.

However, these are without exception solutions in which the salt is formed in solution by combining R-thioctic acid and the appropriate base. The salt itself is not isolated and is thus not in crystalline form. Furthermore, the base is generally used in excess, such that it would not be possible to isolate a pure salt.

Salts of R-thioctic acid with L-lysine and L-arginine are mentioned in Spanish patent 313 056. However, there is no information relating to the production and characterisation of the salts nor any mention of better release and bioavailability of the active ingredient from the dosage forms produced therefrom.

Dosage forms of the racemic thioctic acid with improved bioavailability may also be achieved by their containing the solid salts of thioctic acid instead of the previously used free acid. Here too, bioavailability is surprisingly increased in comparison with the dosage form with the free thioctic acid. The above-stated salt formers may be used as the salt former in this case too. Dosage forms with these solid salts for oral administration are novel and have not hitherto been described. While the salt formers have indeed already been mentioned in general terms in various patents, there has been no discussion of their particular suitability for the production of certain dosage forms.

The present invention also provides all dosage forms containing solid salts of R-thioctic acid which are distinguished by better active ingredient release and better bioavailability than dosage forms prepared from R-thioctic acid. In contrast with the dosage forms prepared from free R-thioctic acid, the dosage forms prepared from salts of R-thioctic acid have not only the advantage of better release and bioavailability of the active ingredient, but are moreover more easily produced:

When producing dosage forms from R-thioctic acid, due to the active ingredient's low melting point of 50.6–50.70° C., the active ingredient is readily sintered both during production of the mouldings and during further processing, for example when applying a taste-masking coating. Sintering of the active ingredient, for example when using slightly elevated temperatures, as are necessary for drying and solidifying the coating, leads to a reduction in porosity, in extreme cases even to complete sintering of the moulding. As a consequence, the moulding (tablet, pellet, granule) dissolves only extremely slowly in the gastro-intestinal tract. This also results in poor bioavailability of the active ingredient. When R-thioctic acid salts are used, there is no sintering and consequently no impairment of bioavailability.

The tendency of free R-thioctic acid to sinter during tablet pressing moreover results in the tablets sticking to the punch if tablets with a relatively high active ingredient content are to be produced on an industrial scale. This may even mean that pressing operations have to be interrupted.

Simultaneously solving the problems of poor active ingredient release and complicated production of dosage form by using the salts of R-thioctic acid instead of the free R-thioctic acid is surprising.

It should be noted in this connection that the two problems of disintegration and dissolution are not directly associated with each other: despite good disintegration behaviour, perfect tablets without sintering phenomena exhibit poor release of the active ingredient R-thioctic acid, as was shown by the above example.

Dosage forms for the salts of R-thioctic acid which may be mentioned are not only tablets, granules, inhalation powders, hard gelatine capsules and pellets, but also soft gelatine capsules, metered aerosols, suspensions, ointments and suppositories, in which the salt is incorporated into a base material, for example into amphiphilic or lipophilic media, polyethylene glycol or propellants.

In comparison with R-thioctic acid, better release from the base material may also be observed in the last-mentioned dosage forms.

The present invention also provides dosage forms containing solid salts of R-thioctic acid. The dosage forms may be used either as a pharmaceutical preparation or as a food additive. The salts may be formed from the salt formers described above and R-thioctic acid. Salts prepared from R-thioctic acid and tromethamine, L-lysine, L-arginine, sodium hydroxide, ammonium hydroxide and creatine are particularly preferred. Production is performed using methods which are generally known in the prior art, as are, for example, described in connection with the racemate of thioctic acid in DE-OS 16 95 358, French patent 4630 M or Example 1.

Analytical values for some of the particularly preferred salts are:

| Acid | Salt former | Melting point |
| --- | --- | --- |
| R-thioctic acid | Tromethamine | 116–118° C. |
| | Sodium hydroxide | 247–257° C. (decomposition) |
| | L-Lysine | 201° C. (decomposition) |
| | None (free acid) | 50.6–50.7° C. |
| Racemic thioctic acid | Tromethamine | 120° C. |
| | None (free acid) | 60.5° C. |

A further advantage may be exploited when optically active salt formers are used:

It is possible to react racemic thioctic acid with the optically active salt former to yield the R- and S-thioctic acid salts. Due to their differing properties, these may be separated and then directly further processed into the dosage forms, wherein it is possible to dispense with any release of R- or S-thioctic acid. Salt formers which may, for example, be used are: L-lysine, L-arginine, D(−)-N-methylglucamine.

The dosage forms are produced using the standard methods which are conventional for this purpose, as are, for example, described in the standard work Sucker, Fuchs, Speiser *Pharmazeutische Technologie,* Thieme Verlag Stuttgart, 1978.

Gastric juice resistance of the dosage forms is achieved either by encapsulating the active ingredient in anionic polymers, for example with a $pK_A$ value of 5.0 to 5.5, and subsequently producing appropriate dosage forms using this encapsulated material. The conventional method for achieving gastric juice resistance of formulations is, however, to coat them with anionic polymers, for example with a $pK_A$ value of 5.0 to 5.5, which do not begin to dissolve until a minimum pH value of 5.0.

Such substances which may be cited by way of example are: shellac, hydroxypropylmethyl cellulose phthalate (commercial product, for example HP 55, manufacturer:

Shinetsu Chemical Company, Tokyo), cellulose acetate phthalate (commercial product, for example Aquateric, manufacturer: FMC Export Corporation, Philadelphia, USA), polyvinyl acetate phthalate, copolymers prepared from methacrylic acid and methacrylic acid esters (commercial products, for example Eudragit L and Eudragit S grades together with Eudragit L 30 D, manufacturer: Röhm Pharma). The dosage forms are produced using the standard methods which are conventional for this purpose, as are for example described in the standard work Sucker, Fuchs, Speiser *Pharmazeutische Technologie,* Thieme Verlag Stuttgart, 1978, and in Bauer, Lehmann, Osterwald Rothgang *Überzogene Arzneiformen,* Wissenschaftliche Verlagsgesellschaft mbH, Stuttgart, 1988.

Gastric juice resistance is tested using USP XXII method <701> Disintegration, wherein the dosage forms must have a resistance to synthetic gastric juice of over two hours, but at least of over 30 minutes.

DETAILED DESCRIPTION OF THE PREFERRED EMBODIMENTS

EXAMPLE 1
Synthesis of Thioctic Acid Salts 1 equivalent of the base is suspended in ethanol, heated to approximately 50° C. and combined with stirring with 1 equivalent of thioctic acid. Stirring is then briefly continued, the solution cooled, wherein the salt slowly crystallises out. Once crystallisation is complete, the salt is filtered out and dried under a vacuum.

EXAMPLE 2
Tablets with 221.3 mg of R-thioctic Acid Sodium Salt, Corresponding to 200 mg of R-thioctic Acid 224.00 g of R-thioctic acid sodium salt, 168.00 g of lactose, 83.40 g of microcrystalline cellulose, 30.24 g of maize starch and 10.08 g of poly(1-vinyl-2-pyrrolidone) are screened, mixed and moistened with purified water. The moistened mixture is then granulated through a perforated screen. The moist granules are then dried in a fluidised bed granulator. 35.32 g of microcrystalline cellulose, 2.24 g of highly disperse silicon dioxide and 6.72 g of magnesium stearate are then screened and mixed with the dry granules. The resultant pressing composition is then pressed into tablets using a tabletting machine.

One tablet weighs 553.3 mg and contains 221.3 mg of R-thioctic acid sodium salt, corresponding to 200 mg of R-thioctic acid.

EXAMPLE 2a

Comparative Example
Tablets with 200 mg of R-thioctic Acid 224.00 g of R-thioctic acid, 168.00 g of lactose, 83.40 g of microcrystalline cellulose, 30.24 g of maize starch and 10.08 g of poly(1-vinyl-2-pyrrolidone) are screened, mixed and moistened with purified water. The moistened mixture is then granulated through a perforated screen. The moist granules are then dried in a fluidised bed granulator. 35.32 g of microcrystalline cellulose, 2.24 g of highly disperse silicon dioxide and 6.72 g of magnesium stearate are then screened and mixed with the dry granules. The resultant pressing composition is then pressed into tablets using a tabletting machine.

One tablet weighs 500.0 mg and contains 200 mg of R-thioctic acid.

EXAMPLE 3
Tablets with 317.4 mg of R-thioctic Acid Tromethamine Salt, Corresponding to 200 mg of R-thioctic Acid 224.00 g of R-thioctic acid tromethamine salt, 168.00 g of lactose, 83.40 g of microcrystalline cellulose, 30.24 g of maize starch and 10.08 g of poly(1-vinyl-2-pyrrolidone) are screened, mixed and moistened with purified water. The moistened mixture is then granulated through a perforated screen. The moist granules are then dried in a fluidised bed granulator. 35.32 g of microcrystalline cellulose, 2.24 g of highly disperse silicon dioxide and 6.72 g of magnesium stearate are then screened and mixed with the dry granules. The resultant pressing composition is then pressed into tablets using a tabletting machine.

One tablet weighs 793.5 mg and contains 317.4 mg of R-thioctic acid tromethamine salt, corresponding to 200 mg of R-thioctic acid.

EXAMPLE 4
Hard Gelatine Capsules with 317.4 mg of R-thioctic Acid Tromethamine Salt, Corresponding to 200 mg of R-thioctic Acid 3.34 g of hydroxypropyl cellulose are first introduced into 34 g of purified water and dissolved by stirring at room temperature. The solution is allowed to stand overnight at room temperature. This solution is the granulating solution. 100.00 g of R-thioctic acid tromethamine salt and 6.66 g of slightly substituted hydroxypropyl cellulose are then screened, mixed and moistened with the granulating solution. The moistened mixture is then granulated through a perforated screen. The moist granules are then dried in a fluidised bed granulator. 4.00 g of magnesium stearate are then screened and mixed with the dry granules. 361.8 mg of the resultant capsule composition are then introduced into size 1 hard gelatine capsules using a capsule filling machine. One capsule contains 317.4 mg of R-thioctic acid tromethamine salt, corresponding to 200 mg of R-thioctic acid.

EXAMPLE 5
Inhalation Powder with 15.87 mg of R-thioctic Acid Tromethamine Salt, Corresponding to 10 mg of R-thioctic Acid 158.7 g of micronised R-thioctic acid tromethamine salt are mixed with 200 g of lactose monohydrate of an average grain size of 100 μm and 35.87 mg of the mixture introduced into size 2 hard gelatine capsules.

The capsules are inserted into conventional commercial powder inhalers and emptied by the patient's inspiratory air.

One capsule contains 15.87 mg of R-thioctic acid tromethamine salt, corresponding to 10 mg of R-thioctic acid.

EXAMPLE 6
Soft Gelatine Capsules with 158.7 mg of R-thioctic Acid Tromethamine Salt, Corresponding to 100 mg of R-thioctic Acid A solution is prepared from 2100 g of medium-chain triglycerides (trade name: Miglyol 812-Neutralöl; manufacturer: Dynamit Nobel) and 700 g of hard fat (trade name: Witeps H 15; manufacturer: Dynamit Nobel). 2000 g of R-thioctic acid tromethamine salt are uniformly incorporated into this solution. The resultant suspension is introduced in the conventional manner into soft gelatine capsules, 380.9 mg of the suspension being used per capsule.

One capsule contains 158.7 mg of R-thioctic acid tromethamine salt.

EXAMPLE 7
Oral Suspension with 7.94% of R-thioctic Acid Tromethamine Salt, Corresponding to 5% of R-thioctic Acid 65 g of highly disperse, amorphous, hydrophobic silicon dioxide (trade name: Aerosil 972; manufacturer: Degussa, Frankfurt), 1 g of ground saccharin sodium and 3 g of ground sodium cyclamate are stirred into 800 g of medium-chain triglycerides (trade name: Miglyol 812-Neutralöl; manufacturer: Dynamit Nobel) and homogenised. After the addition of 1 g of chocolate flavour and 1 g of aniseed flavour, 79.4 g of R-thioctic acid tromethamine salt are stirred in and homogenised.

The suspension is then made up to 1033 g, corresponding to 1 litre, with medium-chain triglycerides and mixed.

5 ml of the suspension contain 397 mg of R-thioctic acid tromethamine salt, corresponding to 250 mg of R-thioctic acid.

EXAMPLE 8

Suppositories with 221.3 mg of R-thioctic Acid Sodium Salt, Corresponding to 200 mg of R-thioctic Acid 404.2 g of R-thioctic acid sodium salt are suspended in 3.376 kg of melted hard fat[1] (see European Pharmacopoeia). Once homogenised, the suspension is poured into 2.3 ml hollow cells and cooled in the conventional manner.

[1] Hard fat is a mixture of mono-, di- and triglycerides of the saturated fatty acids from $C_{10}H_{20}O_2$ to $C_{18}H_{36}O_2$.

One suppository of a weight of 2.07 g contains 221.3 mg of R-thioctic acid sodium salt, corresponding to 200 mg of R-thioctic acid.

EXAMPLE 9

Ointment with 1.11% of R-thioctic Acid Sodium Salt, Corresponding to 1% of R-thioctic Acid 779.5 g of white petrolatum and 30 g of polyoxyethylene (20) stearyl ether (trade name: Brij® 78) are melted together at a temperature of approximately 75° C. 10.89 g of R-thioctic acid sodium salt are suspended into 161 g of viscous paraffin. The melt obtained above is stirred into this suspension. The ointment is then cooled to room temperature while being stirred.

EXAMPLE 10

Metered Aerosol with 3.97 mg of R-thioctic Acid Tromethamine Salt, Corresponding to 2.5 mg of R-thioctic Acid Per Stroke 1000 g of 2 H-heptafluoropropane (=propellant 227) are cooled to a temperature of approximately −55° C. and stirred together with a solution prepared from 11.7 g of polyoxyethylene (25) glyceryl trioleate (trade name: Tagat TO, Goldschmidt AG) in 11.7 g of absolute ethanol. 33.2 g of micronised R-thioctic acid tromethamine salt, 0.9 g of micronised saccharin sodium and 6.75 g of peppermint oil are then added and the resultant suspension homogenised. While still being stirred and cooled, the suspension is made up to 1170.0 g with cooled propellant 227 and then filled into metal cans to be sealed with metering valves which release 100 μl of the suspension per stroke.

3.97 mg of R-thioctic acid tromethamine, salt corresponding to 2.5 mg of R-thioctic acid, are thus released per stroke.

EXAMPLE 11

Pellets with 317.4 mg of R-thioctic Acid Tromethamine Salt, Corresponding to 200 mg of R-thioctic Acid 634.8 g of R-thioctic acid tromethamine salt, 33.2 g of sodium carboxymethyl cellulose and 530.0 g of microcrystalline cellulose are first screened, mixed and moistened with 500.0 g of water and worked to a paste. The moistened mixture is then shaped into strands in an extruder, which are then broken into short cylinders and rounded to pellets in a Spheronizer. The moist pellets are then dried in a fluidised bed drier.

The resultant pellets may be introduced in a quantity of 599 mg into size 0 hard gelatine capsules using a capsule filling machine. One capsule contains 317.4 mg of R-thioctic acid tromethamine salt, corresponding to 200 mg of R-thioctic acid.

EXAMPLE 12

Hard Gelatine Capsules with 158.7 mg of Thioctic Acid Tromethamine Salt, Corresponding to 100 mg of Thioctic Acid 158.7 g of thioctic acid tromethamine salt are mixed with 107.5 g of microcrystalline cellulose, 1.3 g of highly disperse silicon dioxide and 2.5 g of magnesium stearate. The mixture is introduced into hard gelatine capsules in a quantity of 270 mg per capsule.

EXAMPLE 13

Gastric Juice Resistant Tablets with 221 mg of Thioctic Acid Sodium Salt, Corresponding to 200 mg of Thioctic Acid 221 g of thioctic acid sodium salt, 100 g of lactose monohydrate, 100 g of microcrystalline cellulose, 21.5 g of maize starch, 5 g of magnesium stearate and 2.5 g of highly disperse silicon dioxide are mixed and the mixture is pressed into biconvex tablets of a weight of 450 mg and a diameter of 11 mm.

2 g of hydroxypropylmethyl cellulose phthalate (trade name: HP 55, Shinetsu) are dissolved in a mixture of 20 g of absolute ethanol and 30 g of methylene chloride. The solution is sprayed onto the tablets in a conventional manner in a fluidised bed coater, wherein the coater is provided with a closed circuit for solvent recovery and an inert nitrogen atmosphere. After drying, the tablets are tested for gastric juice resistance in accordance with USP XXII, wherein 0.1 N HCl at 37° C. is used as the test liquid. The tablets are sprayed with the above-stated solution and dried until gastric juice resistance is achieved.

EXAMPLE 14

Gastric Juice Resistant Tablets with 200 mg of Thioctic Acid 200 g of thioctic acid are mixed with 100 g of lactose monohydrate, 100 g of microcrystalline cellulose, 20 g of maize starch and the mixture is moistened with a solution of 5 g of Polyvidon K 25 in 60 g of purified water. If necessary, in order to obtain a composition which may be granulated, the mixture is further moistened with purified water and the resultant composition is granulated through a screen with a mesh size of 2 mm. After drying, the granules are passed through a screen with a mesh size of 1 mm and mixed with 5 g of magnesium stearate and 2.5 g of highly disperse silicon dioxide. The mixture is pressed into biconvex tablets of a weight of 432.5 mg and a diameter of 11 mm.

2 g of hydroxypropylmethyl cellulose phthalate (trade name: HP 55, Shinetsu) are dissolved in a mixture of 20 g of absolute ethanol and 30 g of methylene chloride. The solution is sprayed onto the tablets in a conventional manner in a fluidised bed coater, wherein the coater is provided with a closed circuit for solvent recovery and an inert nitrogen atmosphere.

After drying, the tablets are tested for gastric juice resistance in accordance with USP XXII, wherein 0.1 N HCl at 37° C. is used as the test liquid. The tablets are sprayed with the above-stated solution and dried until gastric juice resistance is achieved.

EXAMPLE 15

Tablets with 663 mg of Thioctic Acid Sodium Salt, Corresponding to 600 mg of Thioctic Acid.

1326 g of thioctic acid sodium salt are mixed with 200 g of microcrystalline cellulose, 52 g of maize starch, 8 g of highly disperse silicon dioxide and 14 g of magnesium stearate and the mixture is pressed into oblong tablets of a weight of 800 mg.

The tablets may then be provided in a conventional manner with a coating which is soluble in, permeable to or, in accordance with example 13, resistant to gastric juice.

While the invention has been described in what is presently considered to be the most practical and preferred embodiments, it is to be understood that it is not to be limited by the examples given, but is intended to cover various modifications within the scope of the appended claims. References cited above are hereby incorporated herein by reference.

What is claimed is:

1. A composition for oral administration comprising physiologically compatible solid salts of racemic thioctic acid, with the exception of the calcium salt, aluminium salt and amino acid salt in a quantity of 0.1 mg to 250 mg.

2. A composition according to claim 1, said composition additionally comprising conventional carriers, auxiliary substances and/or diluents.

3. The composition according to claim 1, wherein salt formers are selected from the group of bases consisting of alkali and alkaline earth metals; ammonium hydroxide; and amines of the formula N R1 R2 R3, in which the residues R1, R2 and R3 are identical or different and represent hydrogen, $C_1$–$C_4$ alkyl or $C_1$–$C_4$ oxyalkyl, and alkylenediamines with an alkylene chain of 2 to 6 C atoms.

4. The dosage form according of claim 3, wherein at least one of R1, R2 and R3 is selected from the group consisting of ethylene-diamine or hexamethylenetetramine, pyrrolidone, morpholine, N-methylglucamine, creatine and tromethamine.

* * * * *